(12) United States Patent
Che (10) Patent No.: US 6,653,654 B1
(45) Date of Patent: Nov. 25, 2003

(54) ELECTROLUMINESCENT MATERIALS

(75) Inventor: Chi-Ming Che, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 10/137,272

(22) Filed: May 1, 2002

(51) Int. Cl.[7] .................. C07D 221/02; H05B 33/14; H01L 35/24

(52) U.S. Cl. ................... 257/40; 313/504; 313/506; 428/690; 428/917

(58) Field of Search .............. 257/40, 103; 313/504, 313/506; 428/690, 917

(56) References Cited

U.S. PATENT DOCUMENTS

| | | | |
|---|---|---|---|
| 5,432,014 A | 7/1995 | Sano et al. | 428/690 |
| 6,177,419 B1 | 1/2001 | Campbell et al. | 514/183 |
| 6,310,360 B1 | 10/2001 | Forest et al. | 257/40 |
| 6,316,130 B1 | 11/2001 | Heuer et al. | 428/690 |

OTHER PUBLICATIONS

*Synthesis of metal complexes of 2,0–bis(2–hydroxphenyl)–1, 10–phenathroline and their DNA binding and cleaving activities*, S. Routier et al., *J, Chem. Soc. Perkin Trans. 2*, 1998, 863.

*Blue Electroluminescence in Thin Films of Azomethin–Zinc Complexes*, Y. Hamada et al., *Jpn. J. Appl. Phys.* vol. 32 (1993), pp. L511–L513.

*Highly efficient phosphorescent emission from organic electroluminescent devices*, M.A. Baldo et al., *Nature*, vol. 395, pp. 151–154 (Sep. 11, 1998).

*High–efficiency organic electrophosphorescent devices with tris(2–phenylphyridine)iridium doped into electron–transporting materials*, C. Adachi et al., *Applied Physics Letters*, 77(6), pp. 904–906 Aug. 7, 2000.

Excitonic singlet–triplet ratio in a semiconducting organic thin film, Baldo et al., *Physical Review B*, 60(20), pp. 422–428, Nov. 15, 1999.

*Primary Examiner*—Minh Loan Tran
(74) *Attorney, Agent, or Firm*—Pennie & Edmonds LLP

(57) ABSTRACT

Highly luminous, thermally stable and moisture-resistant light-emitting material derived from quadridentate ONNO-type ligands and a Group 10 metal were employed as emissive dopants in organic light-emitting devices. The dopants have molecular structures represented by the formula I and II:

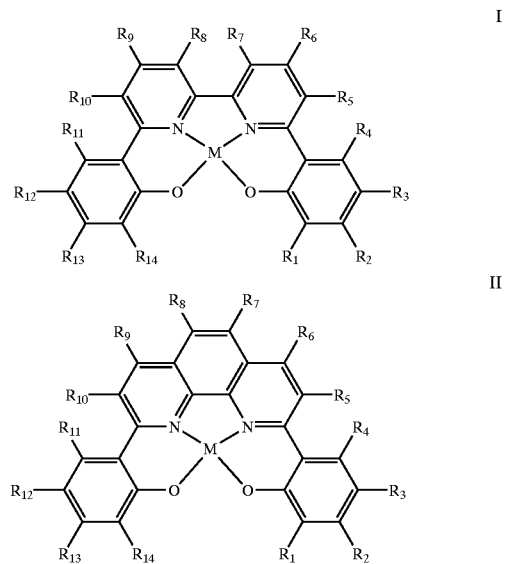

wherein M represents Group 10 metal (including platinum) and $R_1$–$R_{14}$ are each independantly selected from the group consisting of hydrogen; halogen; alkyl; substituted alkyl; aryl; substituted aryl, with substitutents selected from the group consisting of halogen, lower alkyl and recognized donor and acceptor groups.

15 Claims, 8 Drawing Sheets

Schematic diagram of OLED in present invention

Figure 1. Absorption spectra of complexes 1b & 2b in $CH_2Cl_2$

Figure 2. Emission spectra of complex 1b in $CH_2Cl_2$ and as thin film at 298 K Figure 3. Emission spectra of complex 2b in $CH_2Cl_2$ and as thin film at 298 K Figure 4. TGA thermograms of complexes 1b and 2b under nitrogen and air Figure 5. Schematic diagram of OLED in present invention Figure 6. Electroluminescent spectrum, current density-voltage-luminance curves of Device A containing complex 1b (doping level 0.3 wt%)

Figure 7. Electroluminescent spectrum, current density-voltage-luminance curves of Device B containing complex 1b (doping level 1.0 wt%)

Figure 8. Electroluminescent spectrum of Device C containing complex 1b (doping level 2.0 wt%)

ELECTROLUMINESCENT MATERIALS

FIELD OF THE INVENTION

The present invention relates to light-emitting materials, which can be deposited as a thin layer by vacuum deposition, and which can be used as effective dopants in organic light-emitting devices (OLEDs).

BACKGROUND OF THE INVENTION

The progress of light-emitting diode (LED) over the past two decades has primarily focused on inorganic types because early development in organic light-emitting devices (OLEDs) resulted in poor fabrication and packaging, and short lifetimes. Today, gallium arsenide-based LEDs in the market are commonly available with efficiencies in some spectral regions exceeding conventional filtered fluorescent lamps. However, in the development of light-emitting materials for display technology, inorganic semi-conductor materials are not compatible for large-area assembled displays.

Pope et al. at New York University demonstrated organic electroluminescence in the 1960s based on anthracene materials (*J. Chem. Phys.* 38, 2042, (1963)). Much progress have been made since the discovery of the tris(8-hydroxyquinolato)aluminum (Alq$_3$) based thin film device by C. W. Tang et al. at Kodak (*Appl. Phys. Lett.* 51, 913, (1987)). These contributed largely to the continuous discovery of new and improved electroluminescent materials. From small fluorescent molecules to conjugated polymers, many OLEDs have been shown to exhibit sufficient brightness, remarkable efficiencies, good operating lifetimes and desirable ranges of color emission.

Organic light-emitting devices containing metal complexes are of particular interest because of their unusual chemical and electronic properties. Some compounds bearing heavy metals exhibit potential advantages for OLEDs owing to their high internal quantum efficiencies. Conventionally, fluorescent materials are employed as dopants in emissive hosts. Singlet excitons (maximum theoretical internal quantum efficiency=25%) are formed after recombination of hole and electron to emit electroluminescence via dipole-dipole interaction through Forster mechanism (U.S. Pat. No. 6,310,360). Whereas, for heavy metal complexes, strong spin-orbit coupling can lead to singlet-triplet state mixing, which can result in high-efficiency electrophosphorescence in OLEDs (theoretical internal quantum efficiency up to 100%) (*Nature*, 395, 151, (1998); *Synthetic Metals*, 93, 245, (1998); *Appl. Phys. Lett.* 77, 904, (2000)).

However, some phosphorescent materials have intrinsic disadvantages, such as saturation of emission sites due to excessively long lifetimes as well as triplet-triplet annihilation and concentration quenching arising from strong intermolecular interactions at high doping levels (*Phys. Rev. B.* 60, 14422, (1999)).

For example, quadridentate azomethine-zinc complexes have been used as blue light emitters in organic light-emitting devices, which exhibit maximum luminance of approximately 1000 cd/m$^2$ only (*Jpn. J Appl. Phys.*, 32, L511 (1993); U.S. Pat. No. 5,432,014).

Azomethine-aluminum/gallium complexes have been employed in OLEDs as emissive materials. The current density of the device containing azomethine-gallium complex is 1 mA/cm$^2$ at 10 V and the electroluminescence is greenish blue (U.S. Pat. No. 6,316,130).

It is therefore desirable to develop emissive dopant materials that can permit efficient energy transfer between the host and dopant in OLEDs, while causing little or no self-quenching even at sufficiently high doping concentrations.

SUMMARY OF THE INVENTION

Examples of objects of the present invention in embodiments thereof include:

The main objective of this invention is to prepare organic light-emitting devices (OLEDs) doped with new light-emitting materials. The devices exhibit low turn-on voltages and high luminance and efficiencies.

An object of the present invention is to provide thermally stable, moisture-resistant metal-chelated materials that can be deposited as a thin layer of known thickness by a vapor deposition process.

Further, the present invention concerns the design of high luminous dopants, which can be used at low concentration levels in light-emitting devices.

New light-emitting materials derived from quadridentate ONNO-type ligands, and a Group 10 metal (including platinum) were prepared as illustrated by formula I and II:

wherein M represents Group 10 metal (including platinum) and R$_1$–R$_{14}$ are each independently selected from the group consisting of hydrogen; halogen; alkyl; substituted alkyl; aryl; substituted aryl, with substitutents selected from the group consisting of halogen, lower alkyl and recognized donor and acceptor groups.

Embodiments of the present invention includes, but is not limited to, OLEDs comprising heterostructures for producing electroluminescence which contain anode (ITO glass substance), hole transport layer (NPB(α-naphthylphenylbiphenyl amine)), matrix emissive layer [host material (beryllium bis(2-(2'-hydroxyphenyl)pyridine) (Bepp$_2$)) with different concentration of dopants as illustrated by formula I and II herein], charge transport layer (lithium fluoride) and cathode (aluminum metal).

The preferred embodiment as an effective dopant in the OLEDs herein is:

The present invention provides new materials for applications as emissive dopants in electroluminescent devices. The invention includes the synthetic methods for these novel complexes plus their use as light-emitting materials. The devices of the present invention can be applied to field of display, light-emitter, display board for sign lamp, or light source for liquid crystal display.

DETAILED DESCRIPTION OF THE INVENTION

The inventions are generally related to syntheses, spectral characterization, phosphorescence, light-emitting properties of the new light-emitting materials, and their applications in OLEDs. The examples are set forth to aid in an understanding of the inventions but are not intended to, and should not be interpreted to, limit in any way the invention as set forth in the claims which follow thereafter.

The examples given illustrate the synthetic methods of ligands 1a and 2a, and the platinum complexes 1b and 2b. The quadridentate ONNO-type ligands 1a and 2a were prepared by modification of a literature procedure (*J. Chem. Soc., Perkin Trans.* 2, 863, (1998)). Another example of the preparation of ONNO-type ligands has been reported (U.S. Pat. No. 6,177,419).

EXAMPLE 1

Synthesis of 1a

A mixture of 6,6'-bis(2-methoxyphenyl)-4,4'-bis(tert-butyl)-2,2'-bipyridine (1 g) in hydrobromic acid (47%, 20 mL) was refluxed for 12 hours. This was cooled to room temperature and was neutralized with an aqueous saturated $Na_2CO_3$ solution at room temperature. The organic product was extracted with chloroform and the extracts were washed with deionized water (50 mL×2), dried over anhydrous $Na_2SO_4$, and a solid residue was obtained by removal of solvent. Crystalline product of 1a was obtained by recrystallization from a methanol/dichloromethane solution. EI-MS (m/z): 452 [M]$^+$. $^1$H NMR (CDCl$_3$, δ, ppm): 14.45 (2H, s, OH), 8.16 (2H, d, J=1.4 Hz, ArH), 7.97 (2H, d, J=1.3 Hz, ArH), 7.90 (2H, dd, J=8.0 Hz, J=1.4 Hz, ArH), 7.34 (2H, td, J=8.4 Hz, J=1.5 Hz, ArH), 7.07 (2H, dd, J=8.2 Hz, J=1.6 Hz, ArH), 6.96 (2H, td, J=8.1 Hz, J=1.2 Hz, ArH), 1.47 (18H, s, $^t$Bu). $^{13}$C NMR (CDCl$_3$, δ, ppm): 163.3, 159.7, 157.5, 152.2, 131.5, 126.5, 119.2, 118.9, 118.4, 116.4, 35.6, 30.6.

EXAMPLE 2

Synthesis of 1b

The synthetic method of metal complex 1b is described. A mixture of NaOMe (0.014 g, 0.25 mmol) and the ligand 1a (0.113 g, 0.25 mmol) in methanol (20 mL) was stirred for 2 hours. An acetonitrile solution (20 mL) of Pt(CH$_3$CN)$_2$Cl$_2$ (0.25 mmol) was added to the methanolic suspension, which was refluxed for 24 hours. The resulting suspension was filtered and concentrated to about 5 mL. Upon addition of diethyl ether, a brown-yellow solid was obtained. The crude product was recrystallized by diffusion of diethyl ether into a dichloromethane solution to afford yellow crystals. FAB-MS (m/z): 645 [M]$^+$, 1292 (2M$^+$+2), 1938 (3M$^+$+3). $^1$H NMR (CDCl$_3$, δ, ppm): 8.32 (d, 2H, J=1.41 Hz ArH), 8.01

(d, 2H, J=7.25 Hz, ArH), 7.85 (d, 2H, J=1.68 Hz, ArH), 7.48 (dd, 2H, J=7.38 Hz, J=1.13 Hz, ArH), 7.38 (td, 2H, J=5.35, 1.61 Hz, ArH), 6.79 (td, 2H, J=5.40, 1.35 Hz, ArH), 1.54 (s, 18H, $^t$Bu). $^{13}$C NMR (CDCl$_3$, δ, ppm): 162.745, 159.105, 155.291, 149.851, 131.269, 128.005, 124.060, 120.465, 120.402, 116.302, 116.148, 30.402, 29.715. FTIR (KBr, cm$^{-1}$): 3086 w, 2953 m, 1612 w, 1528 s, 1351 s, 1034 m, 885 w, 723 m.

EXAMPLE 3

Synthesis of 2a

In a 100 mL round-bottom flask equipped with a reflux condenser, 2,9-bis(2-methoxyphenyl)-4,7-diphenyl-1,10-phenanthroline (finely ground, 2 g, 3.7 mmol) and pyridinium hydrochloride (4.23 g, 37 mmol) were mixed. The mixture was heated under nitrogen flow to 210° C. for 36 hours. After cooling, water (30 mL) was added and the aqueous solution was extracted with chloroform (3×30 mL). Combined organic extracts were washed with saturated sodium bicarbonate solution (5×30 mL) and water (3×30 mL), dried over anhydrous magnesium sulfate and evaporated to give a bright yellow solid. Chromatography over silica gel using n-hexane: dichloromethane (1:2) as eluent afforded 0.99 g of a yellow solid. FAB-MS (m/z): 517 [M+H]$^+$. $^1$H NMR (300 MHz, CDCl$_3$, δ, ppm): 14.69 (2H, s, OH), 8.52 (2H, s, ArH), 8.41 (2H, dd, J=8.0, 1.3 Hz, ArH), 7.90 (2H, s, ArH), 7.71 (4H, d, J=7.4 Hz), 7.64 (6H, m, ArH), 7.43 (2H, td, J=7.7, 1.5 Hz, ArH), 7.10 (2H, dd, J=7.4 Hz, 1.3 Hz, ArH), 7.04 (2H, td, J=7.5, 1.3 Hz, ArH). $^{13}$C NMR (600 MHz, CDCl$_3$): δ=160.5, 157.7, 150.3, 142.8, 137.8, 132.2, 129.6, 128.9, 128.8, 127.1, 125.7, 123.7, 120.6, 119.4, 119.2, 118.9.

EXAMPLE 4

Synthesis of 2b

K$_2$PtCl$_4$ (0.08 g, 0.19 mmol) and 2a (0.1 g, 0.19 mmol) were refluxed in glacial acetic acid (10 mL) for 2 days. After cooling, the resulting suspension was collected by filtration, washed with acetic acid and water successively and then dried under vacuum to afford a brown solid. The crude product was purified by chromatography on a silica gel column with dichloromethane as eluent. The product was recrystallized by slow evaporation of a dichloromethane solution to afford red crystals. FAB-MS: m/z=710 [M+H]$^+$. $^1$H NMR (270 MHz, DMSO-d$_6$) 8.81 (2H, s, ArH), 8.56 (2H, d, J=8.9 Hz, ArH), 8.01 (2H, s, ArH), 7.86 (4H, m , ArH), 7.71 (6H, dd, J=4.9, 2.0 Hz, ArH), 7.44 (2H, t, J=7.4 Hz, ArH), 7.24 (2H, d, J=8.2 Hz, ArH), 6.80 (2H, t, J=7.6 Hz, ArH).

Figure 1:
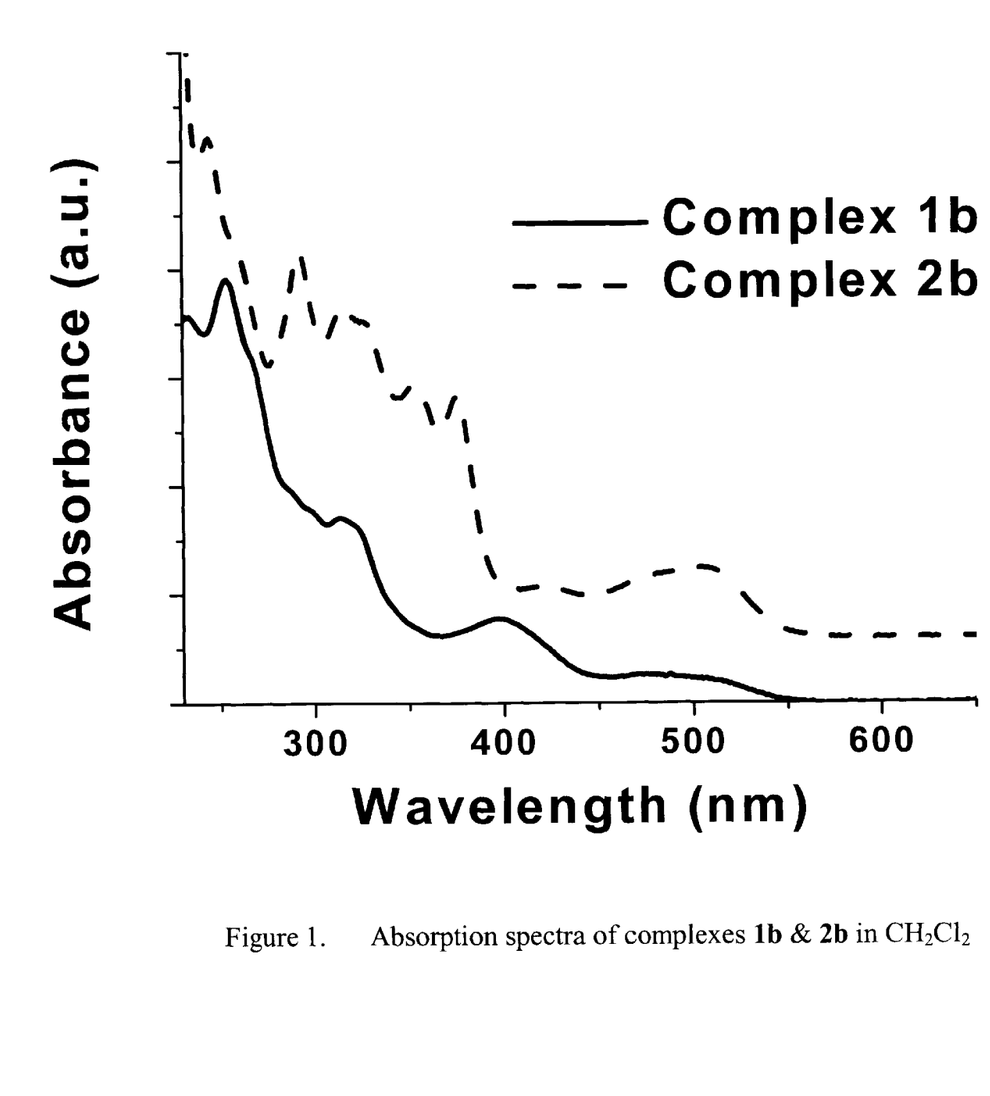
FIG. 1 Absorption spectra of complexes 1b & 2b in $CH_2Cl_2$

The spectral characteristics of the platinum complexes 1b and 2b according to this invention are shown in Table 1. For complex 1b, strong absorption bands at 250–350 nm (ε=38400–17500 dm$^3$mol$^{-1}$cm$^{-1}$) and a moderately intense absorption band at λ$_{max}$ 398 nm (ε=10800 dm$^3$mol$^{-1}$cm$^{-1}$) are observed (FIG. 1). In addition, a broad absorption band can be found at ca. 480 nm (2800 dm$^3$mol$^{-1}$cm$^{-1}$). For complex 2b (FIG. 1), several vibronic transitions at 291–375 nm (ε=39200 to 24700 dm$^3$mol$^{-1}$cm$^{-1}$) and a broad band at 504 nm (ε=7200 dm$^3$mol$^{-1}$cm$^{-1}$) are observed in CH$_2$Cl$_2$.

TABLE 1

UV/vis absorption data of 1b and 2b in CH$_2$Cl$_2$

| Complexes | λ$_{max}$/nm (ε/10$^4$ × dm$^3$mol$^{-1}$cm$^{-1}$) |
| --- | --- |
| 1b | 255 (3.80), 315 (1.75), 400 (0.82), 480 (0.25), 505 (0.22) |
| 2b | 291 (3.92), 315 (3.40), 325 (3.23), 352 (2.58), 375 (2.47), 420 (0.52), 488 (0.67), 504 (0.72) |

Figure 2:
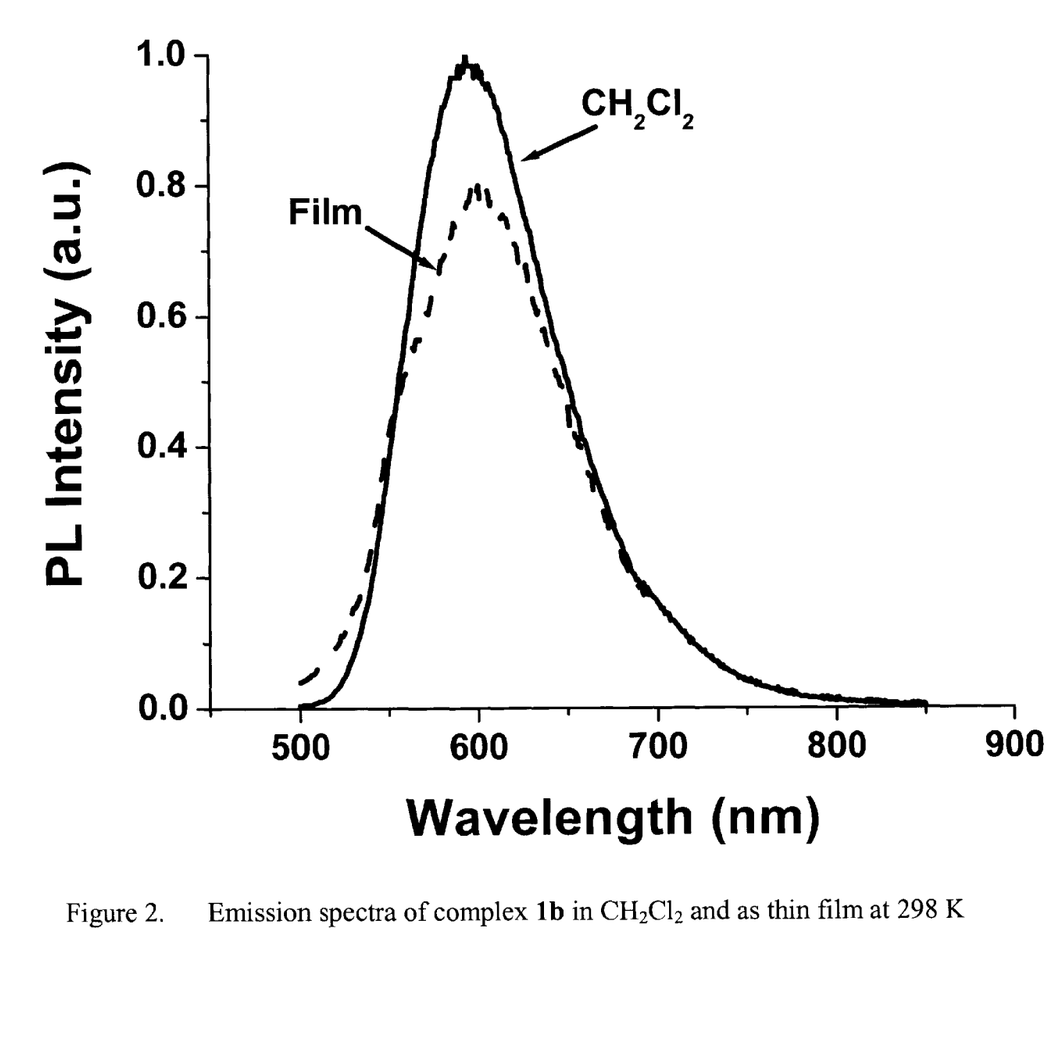
FIG. 2 Emission spectra of complex 1b in $CH_2Cl_2$ and as thin film at 298 K
Figure 3:
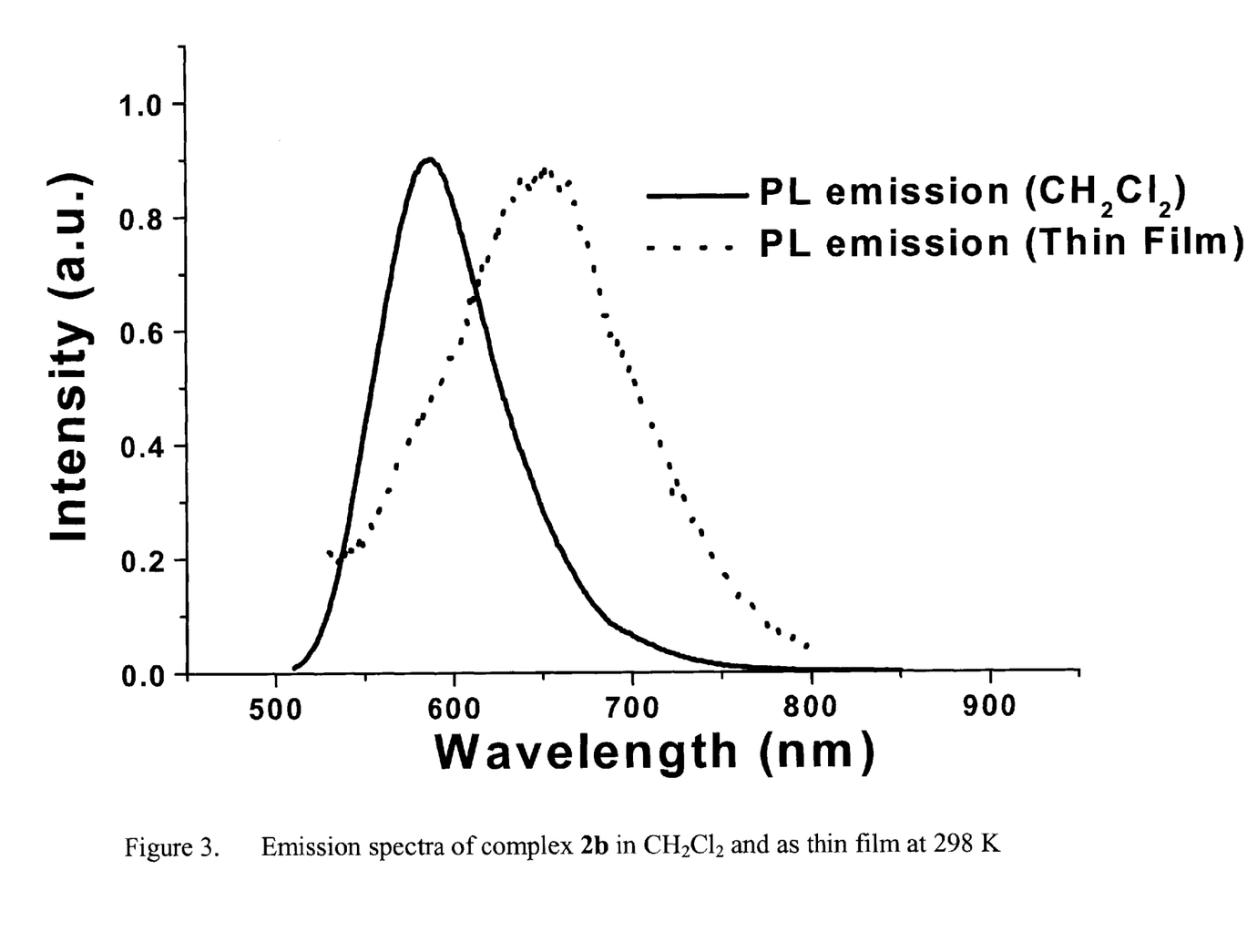
FIG. 3 Emission spectra of complex 2b in $CH_2Cl_2$ and as thin film at 298 K

The photoluminescence (PL) of the platinum complexes 1b and 2b in solution and as thin film are summarized in Table 2. In FIG. 2, the 298 K structureless emission of complex 1b are observed at 595 and 599 nm in CH$_2$Cl$_2$ and as thin film respectively. The PL properties of complex 2b in solution and as thin film are shown in FIG. 3. The emission maximum of 2b in thin film is shifted by 1704 cm$^{-1}$ compared to that in solution. Meanwhile, complexes 1b and 2b exhibit lifetimes of 1.9 and 5.3 μs in CH$_2$Cl$_2$ and luminescent quantum yields of 0.1 and 0.6 (with Ru(bpy)$_3$Cl$_2$ as reference standard) respectively.

TABLE 2

PL properties of complexes 1b and 2b in solution and as thin film

| Complexes (Measuring medium/ Temperature) | Emission (Maximum/nm) | Lifetime (μs) | Quantum yield |
| --- | --- | --- | --- |
| 1b (CH$_2$Cl$_2$/298K) | 595 | 1.9 | 0.1 |
| 1b (Thin Film/298K) | 599 | / | / |
| 2b (CH$_2$Cl$_2$/298K) | 586 | 5.3 | 0.6 |
| 2b (Thin Film/298K) | 651 | / | / | concentration = 1 × 10$^{-5}$ mol dm$^{-3}$

Figure 4:
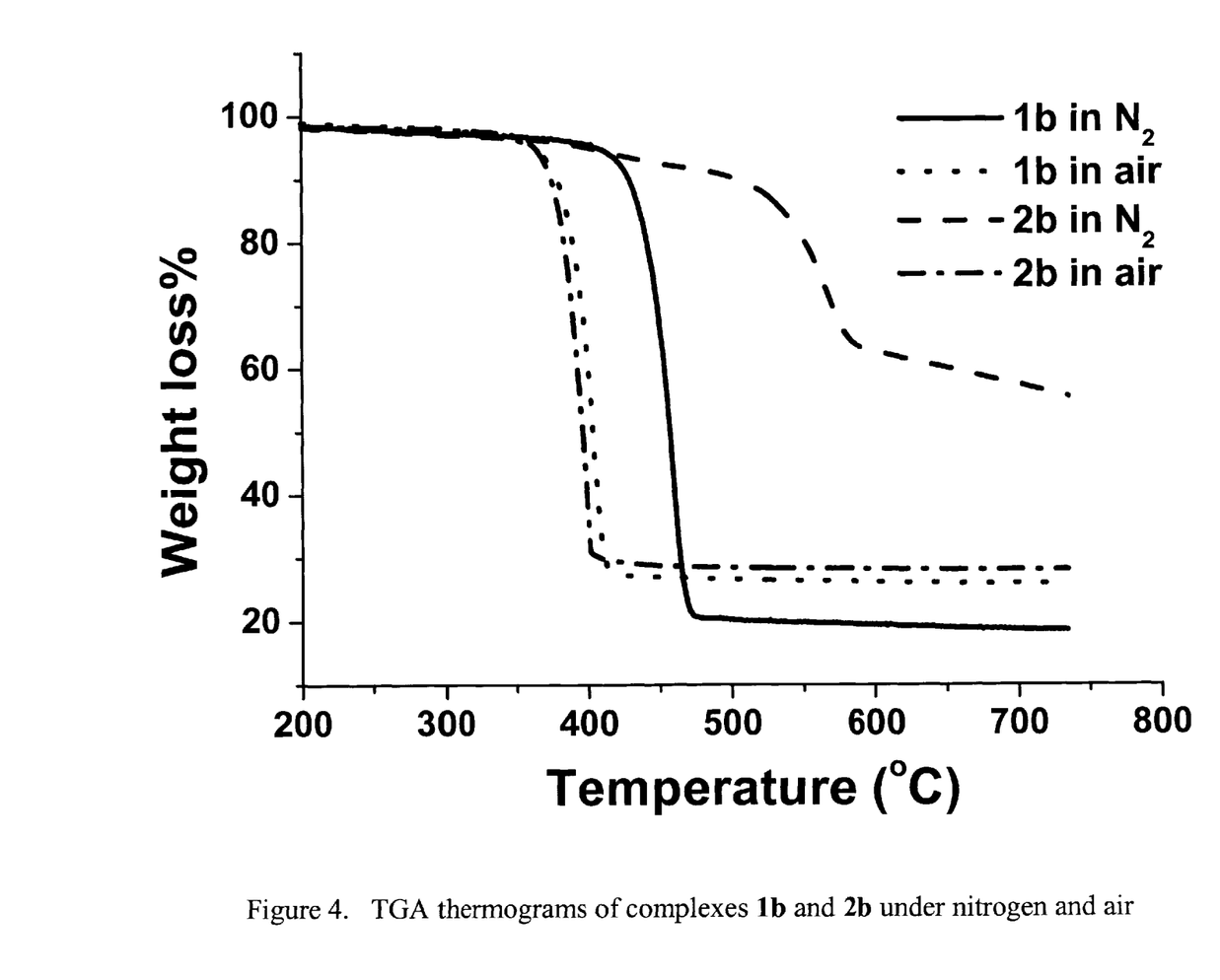
FIG. 4 TGA thermograms of complexes 1b and 2b under nitrogen and air

The TGA thermograms of complexes 1b and 2b are shown in FIG. 4. Both the complexes demonstrate high thermal stabilities in nitrogen and air at heating rate of 15° C./min. Complex 2b is stable up to 536° C. in nitrogen and 379° C. in air. The on-set temperatures of 1b are at 438° C. in nitrogen and 382° C. in air. These observations reveal that these light-emitting materials can be sublimed and stable at vacuum deposition conditions in preparation of OLEDs.

Figure 5:
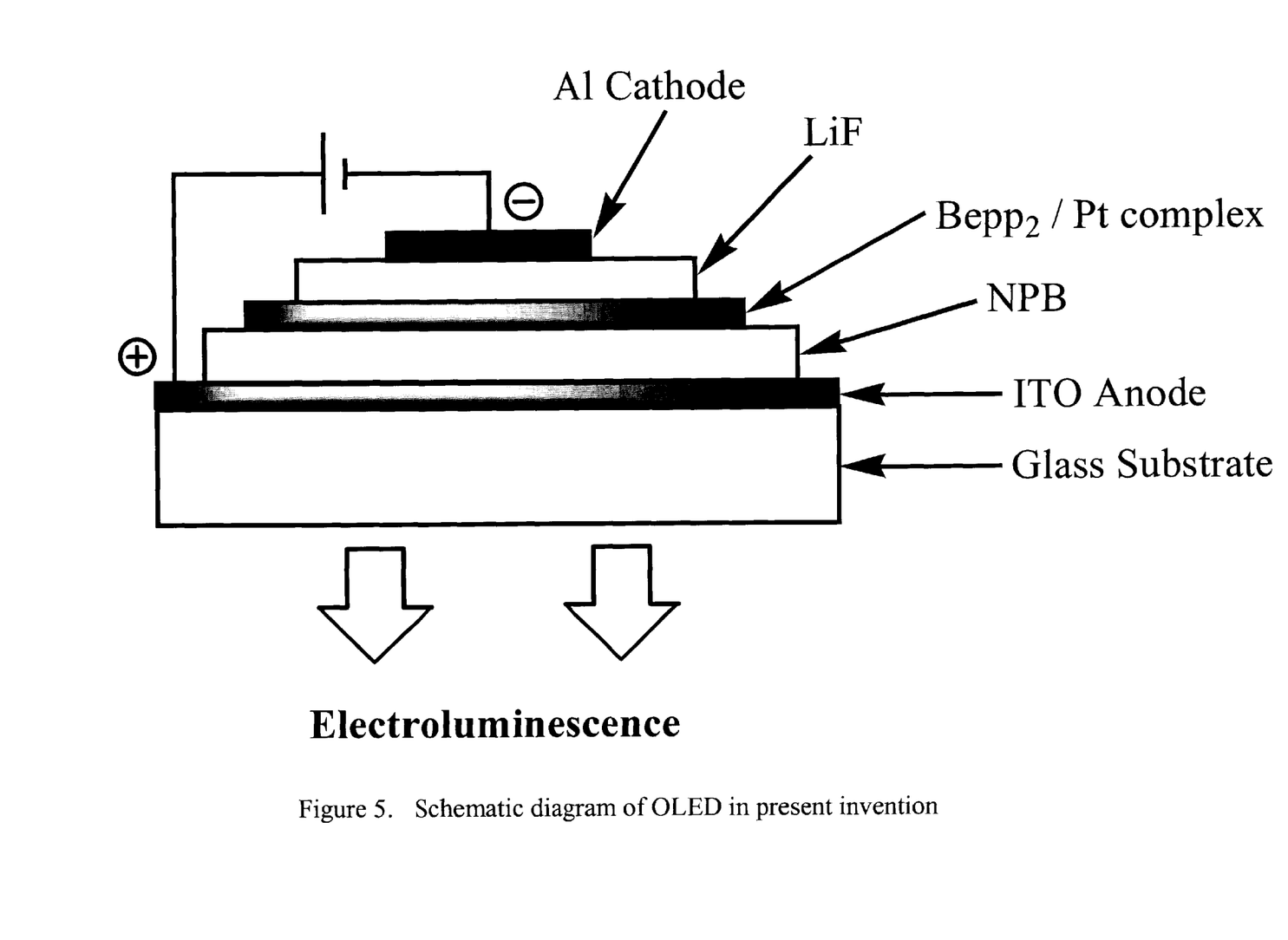
FIG. 5 Schematic diagram of OLED in present invention

An electroluminescent device according to this invention is schematically illustrated in FIG. 5. As examples of the present invention, OLEDs with configurations of ITO/NPB (α-naphthylphenylbiphenyl amine) (500 Å)/[0.3 wt % (device A), 1 wt % (device B), or 2 wt % (device C) of complex 1b]:Bepp$_2$ (400 Å)/LiF (15 Å)/Al (2000 Å) were prepared. The fabrication of device A (0.3 wt % of 1b) follows:

EXAMPLE 5

The device A was assembled as follows: indium tin oxide (ITO) electrode with sheet resistance of 20 Ω/square on glass substrate, a hole transport material NPB (α-naphthylphenylbiphenyl amine) with thickness of 500 Å, an emitting layer made of mixture of 0.3 wt. % complex 1b and blue luminescent material Bepp$_2$ (beryllium bis(2-(2'-hydroxyphenyl)pyridine) with 400 Å thickness, an enhanced charge transport layer LiF with thickness of 15 Å, and aluminum layer with 2000 Å thickness. The metal and organic layers were laminated in sequence under $5 \times 10^{-6}$ mbar without breaking vacuum between different vacuum deposition processes. The layers were deposited at rates of 2 or 5 Å per second. The emissive area of the device as defined by overlapping area of cathode and anode was 3×3 mm$^2$. The ITO coated glass slides were cleaned with organic solvents (acetone-isopropanol-methanol), deionized water, followed by ultra-violet-ozone cleaner. EL spectra and current density-voltage-luminance characteristics of the devices were measured with a spectrophotometer and a computer-controlled direct-current power supply respectively at room temperature.

For these examples, the device external efficiencies increase when the doping concentration levels of complex 1b were adjusted from 2 to 0.3 wt %. The specific examples are further illustrated as follows:

EXAMPLE 6

Figure 6:
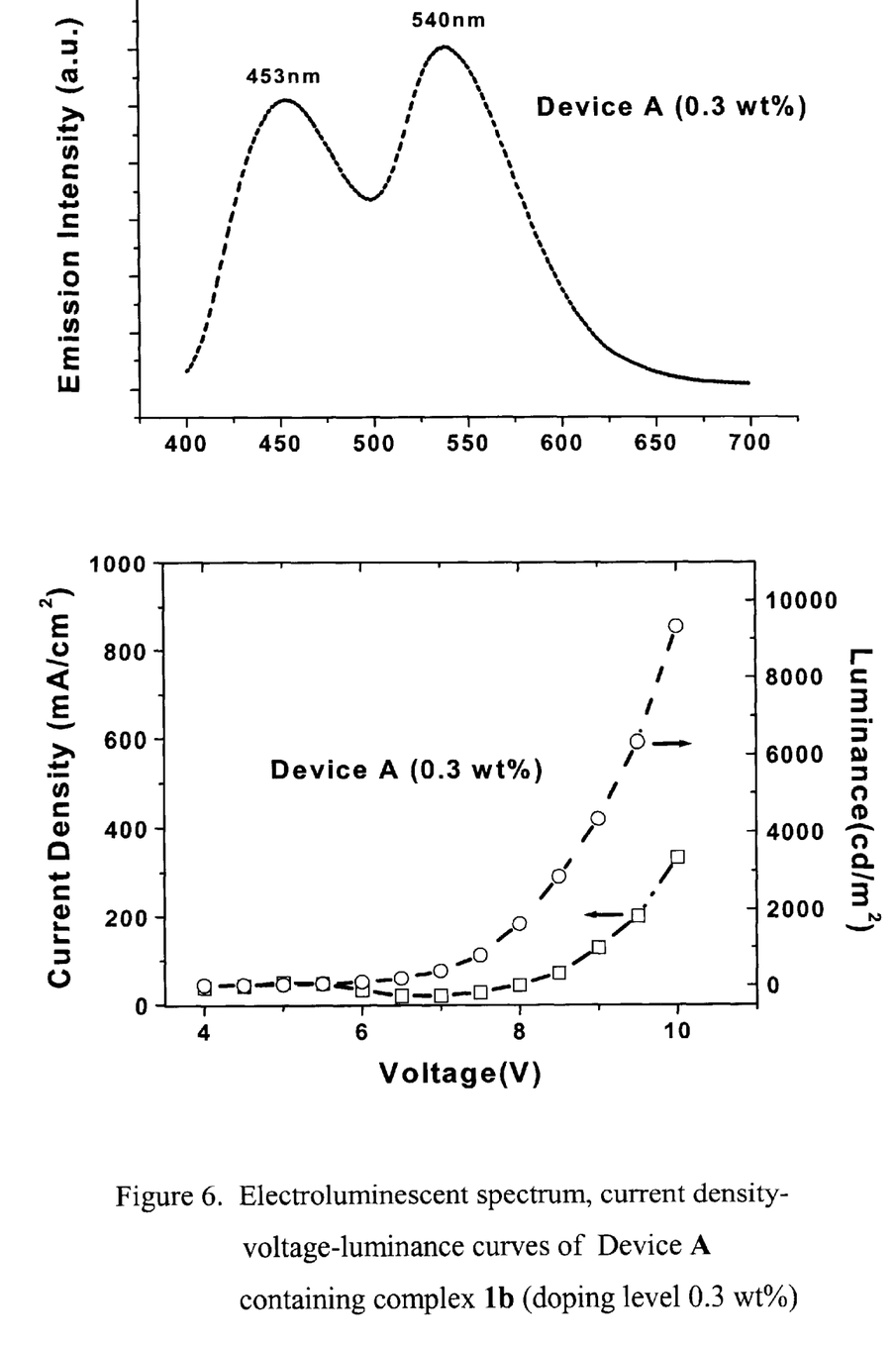
FIG. 6 Electroluminescent spectrum, current density-voltage-luminance curves of Device A containing complex 1b (doping level 0.3 wt %)

The performances of device A with 0.3 wt % doping level of complex 1b are shown in FIG. 6. Two intense EL emissions at 453 and 540 nm are observed when the device was driven under forward bias. The current density-voltage-luminance characteristics curves of device A are also shown. The turn-on voltage is approximately 6–7 V. The maximum efficiency of the device was 4.1 cd/A at luminance of 2849 cd/m$^2$. The maximum luminance of 9325 cd/m$^2$ was obtained at driving voltage of 10 V. The EL color of device A is yellow (CIE coordinates: x=0.33, y=0.47).

EXAMPLE 7

Figure 7:
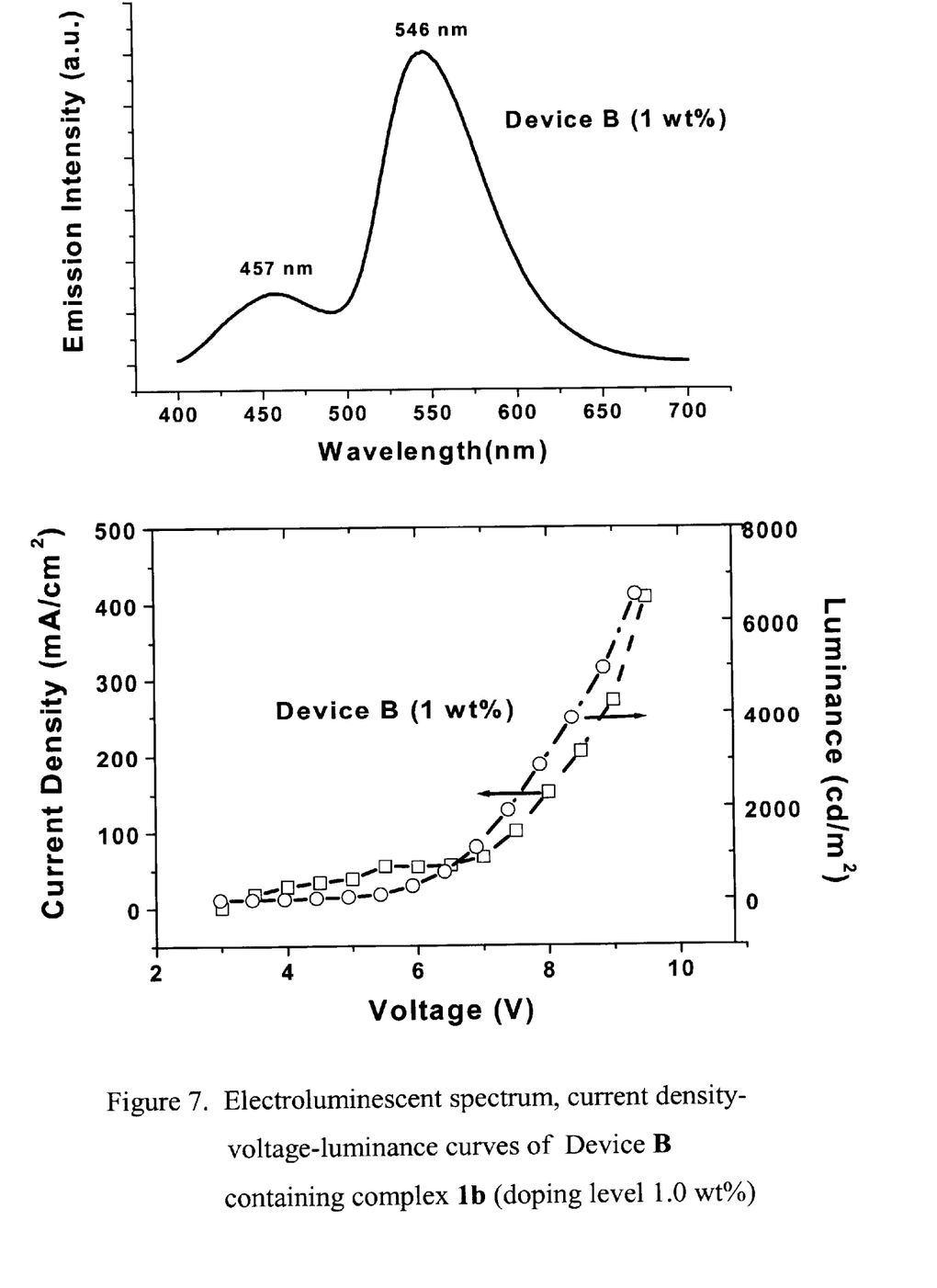
FIG. 7 Electroluminescent spectrum, current density-voltage-luminance curves of Device B containing complex 1b (doping level 1.0 wt %)

The performances of device B with 1.0 wt % doping level of complex 1b are shown in FIG. 7. The device exhibits an intense EL emission peak at 546 nm and a weak emission at 457 nm. The onset voltage of device B was approximately at 6–7 V. The efficiency and maximum luminance were 1.9 cd/A at luminance of 1927 cd/m$^2$ and 6563 cd/m$^2$ at driving voltage of 9.5 V respectively. The EL color of device B is yellow (CIE coordinates: x=0.39, y=0.54).

EXAMPLE 8

Figure 8:
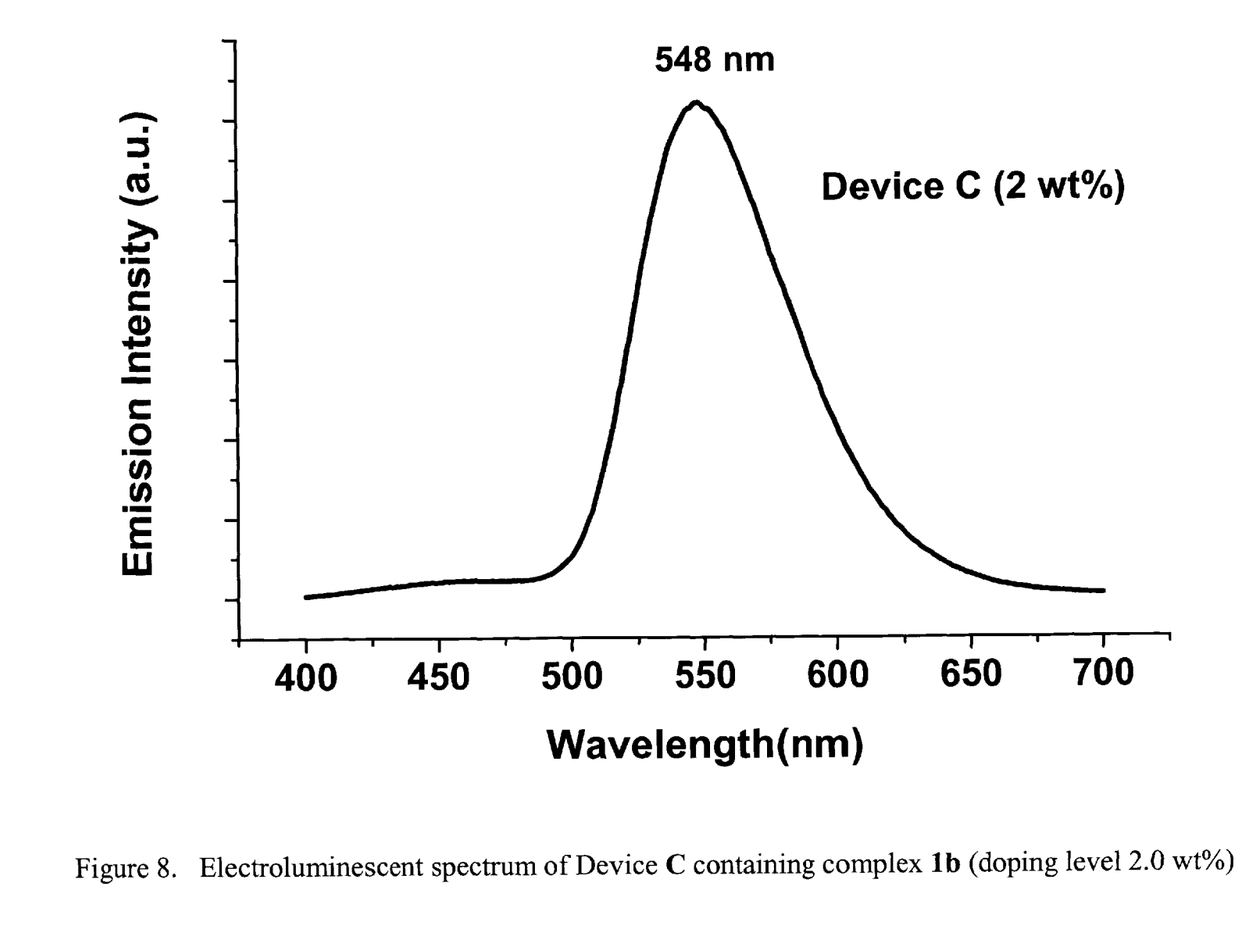
FIG. 8 Electroluminescent spectrum of Device C containing complex 1b (doping level 2.0 wt %)

Device C with 2.0 wt % doping level of complex 1b exhibits an intense EL emission peak at 548 nm with an extremely weak emission at around 450 nm (FIG. 8); EL efficiency of 1.5 cd/A was detected. Luminance of 6450 cd/m$^2$ was observed at driving voltage of 12 V. The EL color of device C is yellow (CIE coordinates: x=0.42, y =0.56).

Typically, doping level of greater than 5% is reported to achieve dopant emission in organic or polymeric light-emitting devices. In this invention, the OLEDs show virtually complete emission of complex 1b when the doping level is around 2% and the efficiencies of devices increase from 1.5 to 4.1 cd/A when the doping levels of complex are decreased from 2.0 to 0.3 wt %.

What is claimed:

1. In an organic light-emitting device containing a heterostructure for producing electroluminescence, an emissive layer, comprising at least a host material and an emissive molecule, present as a dopant in said host material, wherein the said emissive molecule is selected from metal complexes bearing a quadridentate ligand containing at least one pyridine or substituted pyridine group.

2. The emissive layer of claim 1, wherein said emissive molecule is selected from metal complexes bearing a quadridentate ONNO-type ligand, where NN is 2,2'-bypyridine or substituted 2,2'-bypyridine or 1,10-phenanthroline or substituted 1,10-phenanthroline.

3. The emissive layer of claim 1, wherein the metal of said metal complexes is selected from Group 10.

4. The emissive layer of claim 1, wherein said emissive molecule can have a chemical structure represented by Formula I and II:

wherein M represents a Group 10 metal (including platinum) and $R_1$–$R_{14}$ are each independently selected from the group consisting of hydrogen; halogen; alkyl; substituted alkyl; aryl; substituted aryl, with substitutents selected from the group consisting of halogen, lower alkyl and recognized donor and acceptor groups.

5. The emissive layer of claim 4, wherein said emissive molecule is presented as a dopant in said host material in low concentration, including 0.3 to 2.0 weight % based on weight of host material.

6. A method for turning color (CIE coordinates) emitted by an organic light-emitting device comprising emissive layer of claim 5.

7. The emissive layer of claim 4 that produces electroluminescence of yellow color.

8. The emissive layer of claim 4, wherein said the host material is beryllium bis(2-(2'-hydroxyphenyl)pyridine) (Bepp$_2$).

9. The emissive layer of claim 4, wherein the said host material and said emissive molecule can be deposited as a thin layer by method of sublimation or vacuum deposition or vapor deposition or spin-coating or other methods.

10. The emissive molecule is represented by Formula I in accordance with claim 4, wherein the $R_1$–$R_5$, $R_7$–$R_8$ and $R_{10}$–$R_{14}$ groups are proton atoms, $R_6$ and $R_9$ groups are tert-butyl groups, and M is platinum, namely:

11. The emissive molecule is represented by Formula II in accordance with claim 4, wherein the $R_1$–$R_5$, $R_7$–$R_8$ and $R_{10}$–$R_{14}$ groups are proton atoms, $R_6$ and $R_9$ groups are phenyl groups, and M is platinum, namely:

12. A method for the preparation of a light-emitting material having a structure represented by Formula I:

wherein M represents a Group 10 metal (including platinum) and $R_1$–$R_{14}$ are each independently selected from the group consisting of hydrogen; halogen; alkyl; substituted alkyl; aryl; substituted aryl, with substitutents selected from the group consisting of halogen, lower alkyl and recognized donor and acceptor groups.

13. The method in accordance with claim 12 wherein the $R_1$–$R_5$, $R_7$–$R_8$ and $R_{10}$–$R_{14}$ groups are proton atoms, $R_6$ and $R_9$ groups are tert-butyl groups, and M is platinum, namely:

14. A method for the preparation of a light-emitting material having a structure represented by Formula II:

wherein M represents a Group 10 metal (including platinum) and $R_1$–$R_{14}$ are each independently selected from the group consisting of hydrogen; halogen; alkyl; substituted alkyl; aryl; substituted aryl, with substitutents selected from the group consisting of halogen, lower alkyl and recognized donor and acceptor groups.

15. The method in accordance with claim 14 wherein the $R_1$–$R_5$, $R_7$–$R_8$ and $R_{10}$–$R_{14}$ groups are proton atoms, $R_6$ and $R_9$ groups are phenyl groups, and M is platinum, namely:

* * * * *